United States Patent [19]

Manning et al.

[11] Patent Number: 5,378,709

[45] Date of Patent: Jan. 3, 1995

[54] TETRAHYDROPYRIDINE DERIVATIVES FOR THE PREPARATION OF CARDIOPROTECTIVE DRUGS

[75] Inventors: Allan S. Manning, Overijse; Pierre P. Chatelain, Bruxelles, both of Belgium

[73] Assignee: Sanofi, Paris, France

[21] Appl. No.: 214,307

[22] Filed: Mar. 17, 1994

[30] Foreign Application Priority Data

Mar. 18, 1993 [FR] France .................................. 93 03149

[51] Int. Cl.⁶ .............................................. A61K 31/435
[52] U.S. Cl. .................................................... 514/277
[58] Field of Search ...................................... 514/277

[56] References Cited

U.S. PATENT DOCUMENTS

| | | | |
|---|---|---|---|
| 5,026,716 | 6/1991 | Bianchetti et al. | 514/336 |
| 5,109,005 | 4/1992 | Croci et al. | 514/277 |
| 5,229,389 | 7/1993 | Coude et al. | 514/260 |
| 5,270,320 | 12/1993 | Coude et al. | 514/277 |

Primary Examiner—Marianne M. Cintins
Assistant Examiner—T. J. Criares
Attorney, Agent, or Firm—Bacon & Thomas

[57] ABSTRACT

The present invention relates to the use of a 1-(2-naphtylethyl) 4-(3-trifluoromethylphenyl)-1,2,3,6-tetrahydropyridine of formula (I):

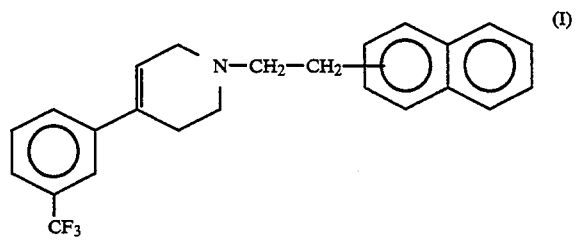

or one of its pharmaceutically acceptable salts, as a cardioprotector.

11 Claims, No Drawings

TETRAHYDROPYRIDINE DERIVATIVES FOR THE PREPARATION OF CARDIOPROTECTIVE DRUGS

The present invention relates to the use of a 1-[2-naphthylethyl]-4-(3-trifuoromethylphenyl)-1,2,3,6-tetrahydropyridine of formula (I):

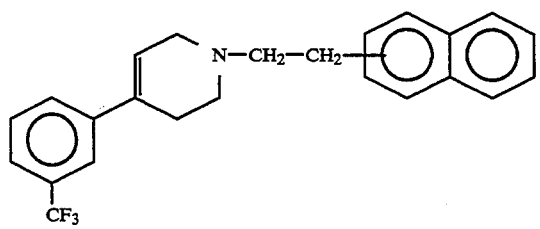

or its addition salts with pharmaceutically acceptable acids for the preparation of cardioprotective drugs.

In formula (I) above, the 1-[4-(3-trifluoromethylphenyl )-1,2,3,6-tetrahydropyridinyl]ethyl group can be bonded in the 1- or 2-position of the naphthalene.

According to a preferred feature of the present invention, this group is bonded in the 2-position of the naphthalene.

The compounds of formula (I), in the form of free bases or addition salts, as well as their preparation and their anorexigenic activity, have been described in European patent application EP-A-101381. Among the pharmaceutically acceptable addition salts of the compound of formula (I), there may be mentioned those formed with mineral acids such as, for example, hydrochloric, hydrobromic, phosphoric and sulfuric acids, or with organic acids such as acetic, formic, propionic, benzoic, maleic, succinic, tartaric, fumaric, citric, glyoxylic, aspartic, methanesulfonic, ethanesulfonic, benzenesulfonic and p-toluenesulfonic acids, etc.

Other therapeutic activities of the compounds of formula (I) have been described more recently, namely the anxiolytic and antidepressant activity (EP- A-369887), anticonstipating activity (EP-A-412901), neurotrophic/neuroprotective activity (EP-A-458696) and anti-free radical activity (EP-A-498718).

It has now been found, totally unexpectedly, that the compounds of formula (I) are also capable of exerting a very valuable cardioprotective activity at low doses.

The cardioprotective activity of the compounds of formula (I) was demonstrated by means of a myocardial necrosis test on rats.

The model used is a modified version of that proposed by G. Rona et al., Arch. Path., 1959, 67, 443–455. It is based on the fact that the administration of high doses of isoprenaline to rats causes very significant myocardial necrosis resembling that found in animals which have suffered a spontaneous myocardial infarction. The myocardial lesions caused by isoprenaline therefore represent a very satisfactory model for studying cardiac necrosis as well as the factors which improve or aggravate it.

CARDIOPROTECTIVE ACTIVITY

Experiment 1

In the model used to evaluate the cardioprotective activity of the compounds (I), the test product was administered orally at different doses once a day for 14 days, the first administration being two hours before a single subcutaneous injection of isoprenaline (40 mg/kg). The control group of animals only receives the single subcutaneous injection of isoprenaline (40 mg/kg). When this period had elapsed, the hearts were removed, weighed and fixed for histological study. The microscopic evaluation of the myocardial lesions and the degree of tissue repair was performed blind by the grid method. The presence of each cell type (healthy or necrotic myocytes, inflammatory cells, fibroblasts) and the presence of collagen fibers are expressed as percentages. The comparison between control group and treated groups was made by calculating the Student "t", for independent values, over the respective distributions of these different cell types.

Thus it was observed that, in the animals treated with doses varying between 1 and 10 mg/kg of 1-[2-(2-naphthyl)ethyl]-4-(3-trifluoromethylphenyl)- 1,2,3,6-tetrahydropyridine hydrochloride, the proportion of myocardial attack induced by isoprenaline (necrotic tissue, presence of inflammatory cells, pyknosis) is significantly lower than that of the controls, and that the proportion of processes corresponding to repair (presence of fibroblasts/fibrocytes and collagen fibers) is likewise significantly less than that of the controls.

Experiment 2

To check whether the cardioprotective action takes effect early on the immediate consequences of isoprenaline, a test was performed by the method described in Experiment 1, the hearts being subjected to a histological study on the 4th day after the injection of isoprenaline, i.e. after only 3 days of treatment.

It was found that the compounds of formula (I) exert a substantial protective effect in this reduced treatment test as well, demonstrating that the cardioprotective activity is already significant on the third day of treatment.

This cardioprotective effect is not associated with a direct effect on the cardiac function: perfusion of the isolated rat heart with 1 $\mu$M of the same compound changes neither the heart rate, nor the ventricular pressure, nor the dP/dt max, nor the cardiac output.

Thus, according to one of its features, the present invention relates to the use of the compounds of formula I above and their pharmaceutically acceptable salts for the preparation of pharmaceutical compositions with cardioprotective action. Within the framework of this use, the compositions prepared in this way exert their cardioprotective action for treating cardiac pathological conditions or for preventing or treating the harmful action of drugs having cardiotoxic side-effects.

More particularly, the present invention relates to the use of the compounds of formula (I) and their pharmaceutically acceptable salts for the preparation of pharmaceutical compositions with cardioprotective action which are intended for the treatment of myocardial infarction, cardiac ischemia, cardiac insufficiency, coronary vasospasms, angina pectoris and prolapse of the heart valves. Furthermore, by virtue of their beneficial intervention in inflammatory processes, the compounds of formula (I) can be indicated for inflammatory pathological conditions of the heart, for example in the treatment and/or prophylaxis of pericarditis and endocarditis.

The compounds of formula (I) can also be used for the preparation of drugs intended for protecting the heart which has already suffered an attack, more particularly for the preparation of drugs intended for preventing a second heart attack.

Moreover, the compounds of formula (I) and their pharmaceutically acceptable salts can be used for the preparation of pharmaceutical compositions intended for preventing or treating the cardiotoxic side-effects of drugs such as anticancer agents, for example those of the anthracycline family such as doxorubicin, and those of the family of the platinum derivatives, such as cisplatin, or the cardiotoxic side-effects of intercalating agents such as elliptinium chloride, natural or synthetic catecholamines and excess caffeine.

Finally, the compounds of formula (I) and their pharmaceutically acceptable salts can be used for the preparation of pharmaceutical compositions with cardioprotective action which are intended for the treatment of obese persons in order to lower the risks of heart attacks, or else for the treatment of patients undergoing heart surgery, for example a transluminai angioplasty or a heart transplant.

Thus, according to another of its features, the present invention relates to a pharmaceutical composition with cardioprotective action which contains, as the active principle, a compound of formula (I) above or one of its pharmaceutically acceptable salts. Preferably, said compositions are in dosage units and the active principle is mixed with the conventional pharmaceutical excipients.

The compounds of formula (I) or their pharmaceutically acceptable addition salts are formulated into compositions for oral, parenteral, sublingual or transdermal administration. The amount of active principle to be administered in order to obtain a cardioprotective effect by the method of the present invention depends on the nature and severity of the complaints to be treated and on the weight of the patient; in the case of combined administration with cardiotoxic drugs, it also depends on the dosage of the latter.

The pharmaceutical compositions of the invention contain an effective amount of at least one product selected from the compounds of formula (I) and their pharmaceutically acceptable addition salts, in association with an inert pharmaceutical vehicle. The unit doses comprise from 2 to 500 mg of active principle, advantageously from 5 to 250 mg and preferably 5 to 150 mg, for example 5, 10, 30, 50, 70, 90, 100, 110, 130 or 150 mg. These unit doses will normally be administered once or several times a day, for example 2 or 3 times a day, preferably once or twice a day, the overall dose in humans varying between 2 and 500 mg per day, for example from 5 to 250 mg and preferably from 10 to 150 mg per day.

For oral or sublingual administration, the active principle is formulated in particular into simple or coated tablets, gelatin capsules containing granules, optionally with delayed release, drops or else liposomes. Lyophilizates or sterile or sterilizable solutions are prepared for intravenous, subcutaneous or intramuscular administration, while conventional patches can be prepared for transdermal administration.

The pharmaceutical compositions according to the present invention can be prepared by customary methods such as those described in EP-101381 or in Remington's Pharmaceutical Sciences, 18th ed., Mack Publ. Co. The active principle can be incorporated into excipients normally employed in these pharmaceutical compositions, such as talc, gum arabic, lactose, cellulose, silica, mannitol, starch, magnesium stearate, aqueous or nonaqueous vehicles, fatty substances of animal or vegetable origin, paraffin derivatives, glycols, various wetting agents, dispersants or emulsifiers, preservatives, etc.

In the pharmaceutical compositions according to the present invention, the active principle of formula (I) can also be in the form of an inclusion complex in cyclodextrins or ethers or esters thereof.

When the compounds of formula (I) or their pharmaceutically acceptable salts are used as cardioprotectors for the treatment of cardiac pathological conditions, the pharmaceutical compositions in which they are present can also advantageously contain one or more other known drugs commonly used in the treatment of these pathological conditions. Among these other drugs, there may be mentioned angiotensin converting enzyme inhibitors such as, for example, captopril, enalapril, fosinopril, quinapril and ramipril; calcium antagonists such as, for example, diltiazem, verapamil, nifedipine, nicardipine and amlodipine; nitro vasodilators such as, for example, nicorandil, trinitrin and isosorbide mononitrate or dinitrate; $\beta$- blockers such as propranolol, sotalol, metoprolol and nadolol; cardiac glucosides such as digitoxin, digoxin and metildigoxin; and thromboxane $A_2$ receptor antagonists.

According to another feature, the present invention relates to a method of inducing cardioprotection in mammals, which comprises administering to said mammal a therapeutically or prophylactically effective dose of a compound of formula I or one of its pharmaceutically acceptable salts.

When the compounds of formula (I) are used as cardioprotectors in the context of a pathological condition in which the heart is at risk as a result of this condition, they will be administered for a period of time dictated by the existence of this condition or of the danger that this condition might recur with harmful effects.

When the compounds of formula (I) are used as cadioprotectors in a treatment with drugs having cardiotoxic side-effects, the period of administration of the compounds (I) will depend on the period of administration of said drugs.

When the compounds of formula (I) or their pharmaceutically acceptable salts are used as cardioprotectors in the case of a treatment with a cardiotoxic drug, they can be formulated separately from the cardiotoxic drug and they may be administered before or at the same time as the cardiotoxic drug or, if necessary, even after the cardiotoxic drug.

In any case, if desired, the compounds of formula (I) and the cardiotoxic drug can be formulated into the same pharmaceutical composition.

The following Examples provide a better illustration of the invention without however implying a limitation; these Examples describe pharmaceutical compositions containing, as the active principle, 1-[2-( 2-naphthyl)ethyl]-4-(3-trifluoromethylpenyl)-1,2,3,6-tetrahydropyridine (which is indicated as Compound A for the sake of convenience), in the form of its hydrochloride.

EXAMPLE 1

Gelatin and titanium dioxide capsules having the following unit composition are prepared:

| Compound A hydrochloride | 54.8 mg |
|---|---|
| Modified cornstarch | 104.72 mg |
| Microcrystalline cellulose | 15.00 mg |
| Anhydrous colloidal silica | 0.16 mg |

-continued

| | |
|---|---|
| Magnesium stearate | 0.32 mg |

EXAMPLE 2

Gelatin and titanium dioxide capsules having the following unit composition are prepared:

| | |
|---|---|
| Compound A hydrochloride | 5.48 mg |
| Modified cornstarch | 142.92 mg |
| Microcrystalline cellulose | 26.00 mg |
| Anhydrous colloidal silica | 0.20 mg |
| Magnesium stearate | 0.40 mg |

EXAMPLE 3

A lyophilizate having the following composition is prepared:

| | |
|---|---|
| Compound A hydrochloride | 13.2 mg |
| Citric acid | 240.00 mg |
| Tween ® 80 | 301.50 mg |
| Mannitol | 1.2001 g |
| 1 N NaOH | 685.00 mg |
| Water for injectable preparations | qsp 30.00 g |

Method of preparation:

The citric acid is dissolved in the water for injectable preparations, and the Compound A hydrochloride is added. After 24 hours, the other components are added and lyophilization is carried out by the customary methods.

EXAMPLE 4

A lyophilizate having the following composition is prepared by the method of Example 3:

| | |
|---|---|
| Compound A hydrochloride | 33.20 mg |
| Hydroxypropylbetacyclodextrin | 751.20 mg |
| Citric acid | 2.10 mg |
| Mannitol | 1509.10 mg |
| Water for injectable preparations | qsp 30.00 g |

We claim:

1. A method for inducing cardioprotection in mammals which comprises administering to a mammal in need thereof a therapeutically or prophylactically effective amount of at least one compound of formula (I):

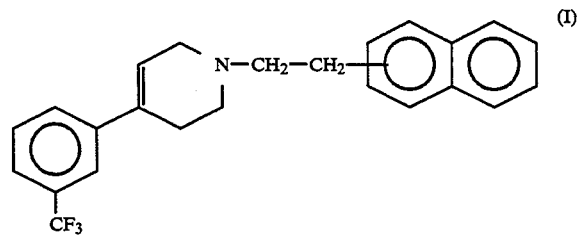

or of a pharmaceutically acceptable salt thereof.

2. A method according to claim 1 in which the compound of formula (I) is 1-[2-(2-naphtyl)ethyl]-4-(3-trifluoromethylphenyl)-1,2,3,6-tetrahydropyridine or a pharmaceutically acceptable salt thereof.

3. A method according to claim 1 in which the compound of formula (I) is 1-[2-(2-naphtyl)ethyl]-4-(3-trifluoromethylphenyl)-1,2,3,6-tetrahydropyridine hydrochloride.

4. A method according to claim 1 in which cardioprotection is induced as a result of myocardial infarction, ischemic heart disease, heart failure, coronary vasospasm, angina pectoris, valvular heart disease.

5. A method according to claim 1 in which cardioprotection is induced for preventing a second heart attack.

6. A method according to claim 1 in which cardioprotection is induced in case of heart inflammatory diseases.

7. A method according to claim 1 in which cardioprotection is induced for treatment or prophylaxis of side-effects caused by cardiotoxic drugs.

8. A method according to claim 7 in which the cardiotoxic drug is an anticancer drug.

9. A method according to claim 8 in which said anticancer drug is an anthracycline.

10. A method according to claim 9 in which said anthracycline is doxorubicine.

11. A method according to claim 1 in which cardioprotection is induced in patients submitted to heart surgery.

* * * * *